United States Patent
Augustine et al.

(10) Patent No.: US 7,001,416 B2
(45) Date of Patent: Feb. 21, 2006

(54) PATIENT COMFORT APPARATUS AND SYSTEM

(75) Inventors: Scott D. Augustine, Bloomington, MN (US); Thomas Peter Anderson, Savage, MN (US); Randall C. Arnold, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 77 days.

(21) Appl. No.: 10/411,865

(22) Filed: Apr. 10, 2003

(65) Prior Publication Data

US 2003/0195596 A1    Oct. 16, 2003

Related U.S. Application Data

(60) Provisional application No. 60/371,314, filed on Apr. 10, 2002.

(51) Int. Cl.
*A61F 7/00* (2006.01)

(52) U.S. Cl. .................... 607/104; 607/96; 607/108
(58) Field of Classification Search ......... 607/107–112
See application file for complete search history.

(56) References Cited

U.S. PATENT DOCUMENTS

| | | | |
|---|---|---|---|
| 3,602,001 A * | 8/1971 | Bauer et al. ................. 62/3.5 |
| 3,950,789 A | 4/1976 | Konz et al. ...................... 2/93 |
| 4,685,442 A * | 8/1987 | Cieslak ....................... 126/204 |
| 5,255,390 A * | 10/1993 | Gross et al. ................... 2/458 |
| 5,350,417 A | 9/1994 | Augustine ................... 607/104 |
| 5,773,275 A | 6/1998 | Anderson et al. ........... 607/104 |
| 5,800,489 A | 9/1998 | Augustine ................... 607/107 |
| 5,970,519 A | 10/1999 | Weber ............................. 2/81 |
| 6,178,562 B1 * | 1/2001 | Elkins ........................... 2/458 |
| 6,375,673 B1 * | 4/2002 | Clifton et al. ............... 607/104 |
| 6,596,019 B1 * | 7/2003 | Turner et al. ............... 607/108 |
| 6,695,872 B1 * | 2/2004 | Elkins ........................ 607/104 |

* cited by examiner

*Primary Examiner*—Henry M Johnson, III
(74) *Attorney, Agent, or Firm*—Incaplaw; Terrance A. Meador (57) ABSTRACT

Apparatus and a system for thermally comforting a patient include pneumatic, convective device providing thermal treatment for persons or animals. The pneumatic convective device is adapted to fit around a person's neck and provides convective warming focused or directed primarily on the thorax or body core. The pneumatic convective device includes an inlet, a region in distribution with the inlet for distributing a stream of pressurized, thermally treated air, and a permeable member for emitting pressurized, thermally treated air from the distribution region.

19 Claims, 8 Drawing Sheets

PATIENT COMFORT APPARATUS AND SYSTEM

CROSS REFERENCE TO RELATED APPLICATIONS

This application claims the benefit of U.S. Provisional No 60/371,314 filed Apr. 10, 2002.

This application contains subject matter related to that of U.S. patent application Ser. No. 10/411,431, for "FORCED AIR WARMING UNIT" and PCT Patent Application Serial No. PCT/US03/11128, for "PATIENT COMFORT APPARATUS AND SYSTEM", filed concurrently with this application, and to that of U.S. Design patent application Ser. No. 20/179,545, for "FORCED AIR WARMING UNIT", now U.S. Pat. No. D485,338.

BACKGROUND OF THE INVENTION

1. Field of the Invention

The invention is directed to a patient comfort system that includes pneumatic convective devices receivable on a human or animal body which receive a stream of pressurized, thermally conditioned air, distribute the pressurized air within a pneumatic structure, and emit the air through one or more surfaces for convective transfer of heat between the thermally conditioned air and the body. In particular, the invention is directed to the warming of human or animal bodies in a clinical setting by providing thermal treatment to wearers of the system while permitting movement of the user and enhancing clinical convenience.

2. Description of the Related Art

Pneumatic devices which transfer heat between thermally-conditioned air and a body are known. For example, there are inflatable pneumatic devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These inflatable devices are typically characterized as "blankets" or "covers". Arizant Healthcare Inc., the assignee of this application, makes and sells such devices under the BAIR HUGGER® brand. One such device is the Model 522 Upper Body Blanket.

Inflatable pneumatic warming blanket or cover devices are adapted especially for use with supine persons and are typically deployed by being laid directly on a person lying on a bed, a gurney, or a surgery platform, so as to drape over or cover some portion of the person. Because these devices are designed to cover and hang about or over a supine person, they are not easily or readily deployed on persons who are standing, sitting, reclining or moving. In particular, inflatable blankets are not suitable in a clinical setting in which it is desirable to warm a patient, and also necessary that the patient be able to move about and between various postures. In addition, there are a variety of clinical settings in which patient warming is desirable, with each setting requiring its own unique access to patient anatomy that may not be afforded by an inflatable blanket. For example, examination or treatment of a patient in a primary acute care unit (PACU) could call for access to patient lines in the chest area, setting IV's in the arm, application of a stethoscope to the back and/or side, or application of a blood pressure cuff. Further, patient mobility throughout a clinic or a hospital is highly desirable, but would be severely curtailed with use of inflatable blankets. For example, transporting a patient to an x-ray or MRI location in a wheelchair, would be made problematic with an inflatable blanket.

There is also an advantage in not changing established and familiar algorithms of care in which both patients and nurses deal with clinical garments, such as gowns, and nurses know how to deliver care in all circumstances where a patient is wearing a clinical garment. If an inflatable blanket were to be used for warming, a new algorithm would be required to deal with this new element in clinical practice.

One attempt to adapt an inflatable pneumatic blanket for non-supine postures is embodied in U.S. Pat. No. 5,697,963, assigned to Augustine Medical, Inc. and incorporated by reference. In this adaptation, an inflatable pneumatic blanket having a head-section drape is provided with an aperture in the head section drape that is large enough to accommodate the head of a person sitting in a chair. However, this adaptation has a limited use in that a person using it must remain in a sitting or reclining posture in order for the device to drape over the person's body and retain warmed air and heat about the person. Such devices are not designed to accommodate movement or changes in the person's posture or to allow easy access to patient anatomy. These devices are meant to treat hypothermia by driving calories into the patient.

Other inflatable pneumatic warming devices designed for use with supine persons employ tubular structures to at least partially surround a person, and utilize sheets of material extending across the person and the structures to retain warmed air and heat about the person. These devices are even less adaptable than blanket devices for non-supine uses. See, for example, U.S. Pat. Nos. 5,300,101 and 5,674,269, which are incorporated by reference.

A need exists for a pneumatic convective device that achieves the objectives of increased comfort, reduced shivering, and treatment or prevention of hypothermia in a clinical or medical office setting where patients must be able to change postures and enjoy a certain amount of mobility without a significant impact on or change to the treatment algorithm. For example, when visiting a physician for an examination, a patient may be ushered into an examination room, asked to remove clothing in order to permit examination, and given a thin cloth gown to wear while awaiting the physician. In this environment, the patient may be chilled, may shiver, or may be in a condition conducive to hypothermia. Patient anxiety is frequently exacerbated by this cold discomfort. Concomitant with a heightened level of anxiety, patients perceive time as slowing and this anxious waiting period can seem to be prolonged. The cold discomfort can cause a one hour wait to seem like 2 hours to the patient. People tend to vasoconstrict when frightened, and vasoconstriction can lead to reduced peripheral temperature and increased blood pressure, and can make IV access much more difficult. Finally, there is evidence that feeling cold increases the perception of pain. A thin cloth gown provides little in the way of insulation, warmth, and comfort in such circumstances. Therefore, in addition to the patient satisfaction and comfort produced by a bath of thermally-treated air, providing warmth to a cold patient in a medical setting should produce the following unexpected benefits: 1.) reduced blood pressure and easier IV access; 2.) reduced pain sensation; 3.) normalizing of the patient's perception of time slowing; 4.) reduced anxiety and reduced need for medication. These and other objectives are realized when a patient is maintained in a state of "thermal comfort."

It would be advantageous to provide a course of action, a method, or an instrument by which a patient could be maintained in a state of thermal comfort characterized by a comfortable, healthy temperature while awaiting the physician and even while undergoing examination or treatment. An inflatable blanket or cover could be deployed for this purpose, but would be very impractical because the patient would be required to remain supine or maintain a prone or sitting position. Clinical convenience and utility dictate a more flexible solution in which a pneumatic, convective device serves a warming function in one or more forms that permit movement of the user and of the device itself on the user for examination. It would be particularly advantageous if the solution comported with present modes of treatment that presume the use of clinical garments. For optimal heating, such forms should focus or concentrate the convective effect on the portion of a body being warmed that has the highest concentration of cutaneous thermal receptors. This portion includes the head, neck, chest and abdomen.

Pneumatic devices that thermally condition persons while standing and/or moving are known. One such device, described in U.S. Pat. No. 4,457,295 incorporates a pneumatic, convective means into an article of clothing that is intended for heavy-duty use in an unfriendly environment. The objective of this device is to warm and ventilate by general application of pressurized, heated air through the inside of a closed article of clothing. The pressurized, heated air is provided through a valve system from a source that is convenient to a particular unfriendly environment, such as an exhaust manifold of a motorcycle engine. The article of clothing is fitted to the wearer's body and is closed in order to afford protection against the environment in which the device is deployed. Thus, the device further requires a means for ventilating moisture from within the article of clothing. Its normally closed configuration and complicated pneumatics make this device inconvenient and impractical to use for patient comfort in a clinical environment.

A pneumatic garment, described in U.S. Pat. No. 3,468,299, includes a hooded overcoat intended to be used in unfriendly environments for heating and ventilating a person. This device's structure and operation make it also unsuitable for use in maintaining patient comfort in a clinical environment.

SUMMARY OF THE INVENTION

The invention provides pneumatic convective thermal treatment of the feeling of being cold by means of pneumatic convective for use on a patient in a clinical setting. The invention includes a pneumatic convective device, as well as a system and method employing such a device to maintain comfort a patient by warming. The pneumatic convective devices provide effective convective warming that is focused or directed primarily on or to the most thermally sensitive regions of a user. These devices are also simple to manufacture, store, and deploy for use. Finally, because this invention is meant to produce or induce a state of thermal comfort in a patient, without providing hypothermia therapy, airflow exiting the pneumatic convective device of less than 15 CFM (cubic feet per minute) and a temperature of less than 105° F. are preferred.

DETAILED DESCRIPTION OF THE PREFERRED EMBODIMENTS

The invention is embodied as a pneumatic convective device receivable on a human or animal body in a clinical setting which receives a stream of pressurized, thermally conditioned air, distributes the pressurized air within a pneumatic structure, and emits the air through one or more surfaces for convective transfer of heat between the thermally conditioned air and the body. Various specific embodiments of the invention are illustrated and discussed according to an example in which a human body is warmed by focusing or concentrating convective warming on the body core in order to permit patient movement and to enhance clinical convenience, although this is not intended to suggest that the invention may not be used for cooling, which, indeed, it may. The pneumatic convective device may be deployed for use with humans, animals, patients, clinicians, practitioners, observers, and so on.

Further, use of the term "convective" to denote the transfer of heat to a body refers to the principal mode of heat transfer, it being understood that heat may at the same time be transferred between a device according to this invention and a body by conduction and radiation, although not to the degree of convection.

The pneumatic convective device has a pneumatic portion for receiving and distributing at least one stream of pressurized, thermally conditioned air in a structure for being disposed on, adjacent, or next to the core, thorax, or chest of a body.

The embodiments of the invention illustrated and discussed below are inflatable. That is, their structures, flaccid when not in use, tauten when receiving a stream of pressurized air. The illustrations portray these structures in both inflated and uninflated states, with the understanding that inflation of these embodiments is not necessary to practice of the invention. Indeed, as consideration of the embodiments will make clear, inflatability itself is not necessary to practice of the invention.

FIGS. 1A–1K illustrate an exemplary pneumatic convective device which embodies the invention. The device 150 is formed by sealing together two sheets 160 and 162, at least one of which is permeable. In this case, the sheet 160 is permeable, with its permeability represented by apertures 166. The sheets 160, 162 are sealed together continuously along their peripheries 168, with a rather wide uninflatable region 169 extending from the peripheries inwardly of the sheets. Within a distribution region 170 surrounded by the uninflatable region 169, the sheets are sealed together intermittently at a plurality of locations 172. An opening or inlet port 163 is provided through the sheet 162, and a quadrilateral hose card 164 with a hole is mounted to the sheet 162 over the inlet port 163, with the hole in the hose card 164 aligned with the inlet port 163. The inlet port 163 may receive the end of an air hose from which a stream of pressurized, thermally-treated air flows into the space between the sheets 160 and 162. At least one of the sheets 160 and 162 is permeable to air. In this example, only the sheet 160 is air permeable, although this is not intended to so limit the scope of the invention. The permeability of the sheet 160 may be provided by characteristics of the material from which it is formed; alternatively, holes or apertures 166 may be formed in it during the process which joins the sheets 160 and 162. Or, permeability of the sheet 160 may result from the characteristics of its formative material and from formed apertures.

Figure 1A:
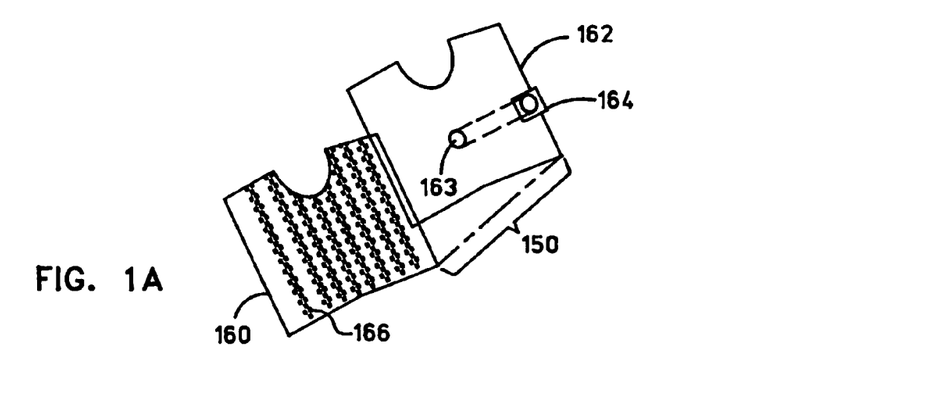
FIGS. 1A–1C illustrate a pneumatic convective device according to an embodiment of the invention as an inflatable bib.
Figure 1B:
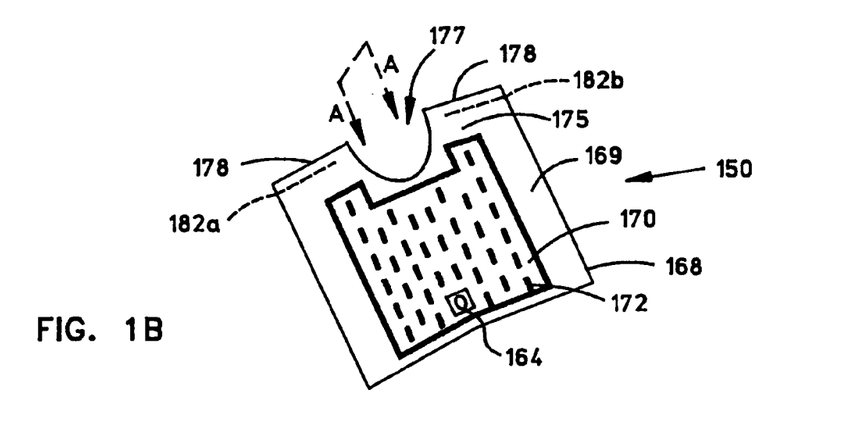

A U-shaped indentation 177 is formed at one end of the device 150, with an open margin along the upper edge 178 of the device 150. As thus far described, the device 150 may be disposed over the chest region of a user, with the sheet 160 facing the user, and the user's neck received in the indentation 177. In this disposition, the device is operated for its intended purpose when the end of an air hose is received in the hole of the hose card 164. A stream of pressurized, thermally treated air flowing through the end of the air hose into the device inflates and is distributed through the distribution region 170, and is emitted through the permeable sheet 160 in the direction of a user's chest. When held in position against, adjacent to or over a user's chest by elements described below, a hospital gown may be put on the user in the usual fashion so that the device 150 is positioned between the user's chest and the gown. Alternatively, the pneumatic device may be placed over the patient's gown or shirt much like a bib.

The elements for maintaining the device 150 disposed against a user's chest with the user's neck received in the indentation 177 all act between the user's neck and the device, in the area of the indentation 177. One such element is a pair of tie straps 180a and 180b flanking the open end of the indentation. These straps may be provided integrally with the device 150 by means of two lines of weakness 182a and 182b formed in the uninflatable region 169, displaced inwardly from the upper edge 178. The straps 180a and 180b may be freed as shown in FIG. 1D to provide two ends for tying together behind as user's neck. FIG. 1E shows two release liners 183a and 183b exposing adhesive layers to attach the device 150 to patients' clothing/person. FIG. 1F shows a line 190 with two end clips 191 attachable to the device 150 at either side of the indentation 177. FIGS. 1G and 1H show the device 150 somewhat elongated so that it extends to the knees of a user. In this regard, the device resembles the inflatable thermal blanket disclosed and claimed in U.S. Pat. No. 5,697,963. This device is distinct from the blanket of the '963 patent in that it does not include the various draping features of the '963 blanket. In FIGS. 1G and 1H, an aperture 192 is formed in the portion 169a of the uninflatable region 169 that abuts the top edge 178. A longitudinal line of weakness 194 is formed in the uninflatable region 169a, running from the upper edge 178 to the aperture 192, and two lateral lines of weakness 196a and 196b are formed in the uninflatable region portion 169a, displaced inwardly from the upper edge 178. The uninflatable region may be cloven into two opposing sections that may be separated to receive the neck of a user. Two straps 198a and 198b may be realized by tearing the uninflatable region portion 169a along the lines of weakness 196a and 196b and tied behind the neck of the user to retain the device 150 for use. Instead of straps, the two opposing sections yielded by cleaving the sealed section along the line of weakness 194 may be releasably held together by other mechanisms such as hook and eye elements 199a and 199b, as shown in FIG. 1I, as well as by clips, Velcro buttons, string, snaps, repositionable adhesive, double-sided adhesive, hook and loop, rivets, and any and all equivalents thereof.

The embodiment of the pneumatic convective device illustrated in FIGS. 1A–1J and described above, has a distribution region 170 for distributing a stream of pressurized air, the inlet 163 is in communication with the distribution region 170 for receiving a stream of pressurized air, a permeable member (sheet 160) for emitting pressurized air from the distribution region, a region 169 in which air is not distributed, an indentation 177 or opening 192 in the region 169 for receiving the neck or head of a person and a mechanism 180a/180b, 183a/183b, 190/191, 198a/198b, 199a/199b, and any and all equivalents acting with the indentation 177 or opening 192 for releasably retaining the pneumatic convective device against the neck of a person.

An air hose end may be adapted for use with the pneumatic convective device embodiments described herein. The air hose end may be in the form of an elongate cylinder or frusto-conical section. Materials for this form are well known and include, for example, hard molded plastic. Such a hose end is describe below in relation to FIGS. 2A–2D.

Figure 1C:
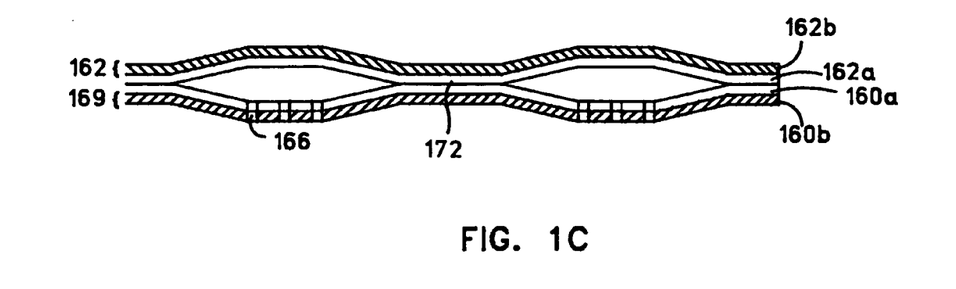
Figure 1D:
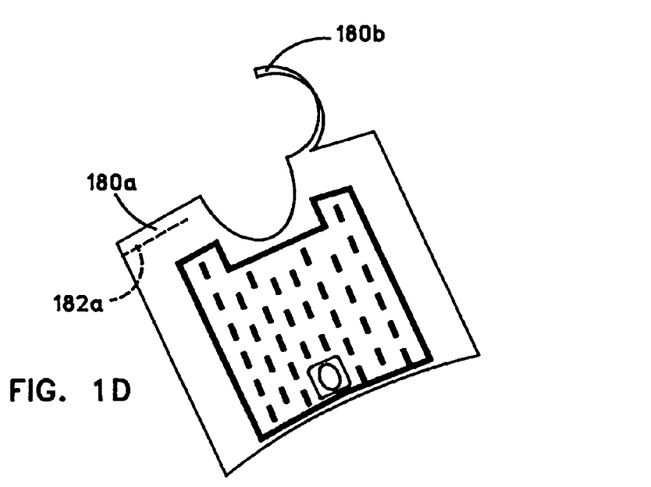
FIGS. 1D–1I illustrate various elements for engaging the device of FIGS. 1A and 1B about the neck of a user.
Figure 1E:
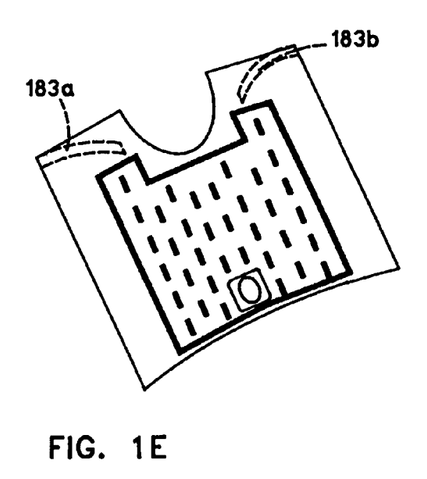
Figure 1F:
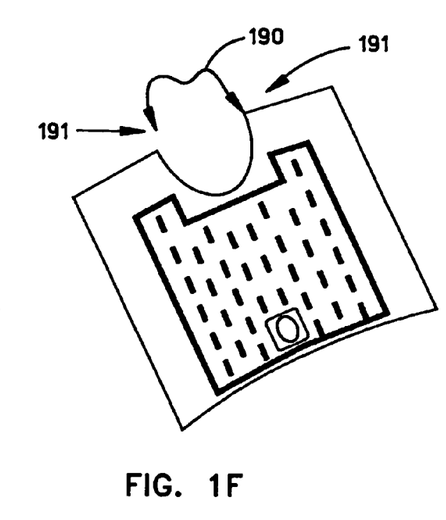
Figures 1G, 1H:
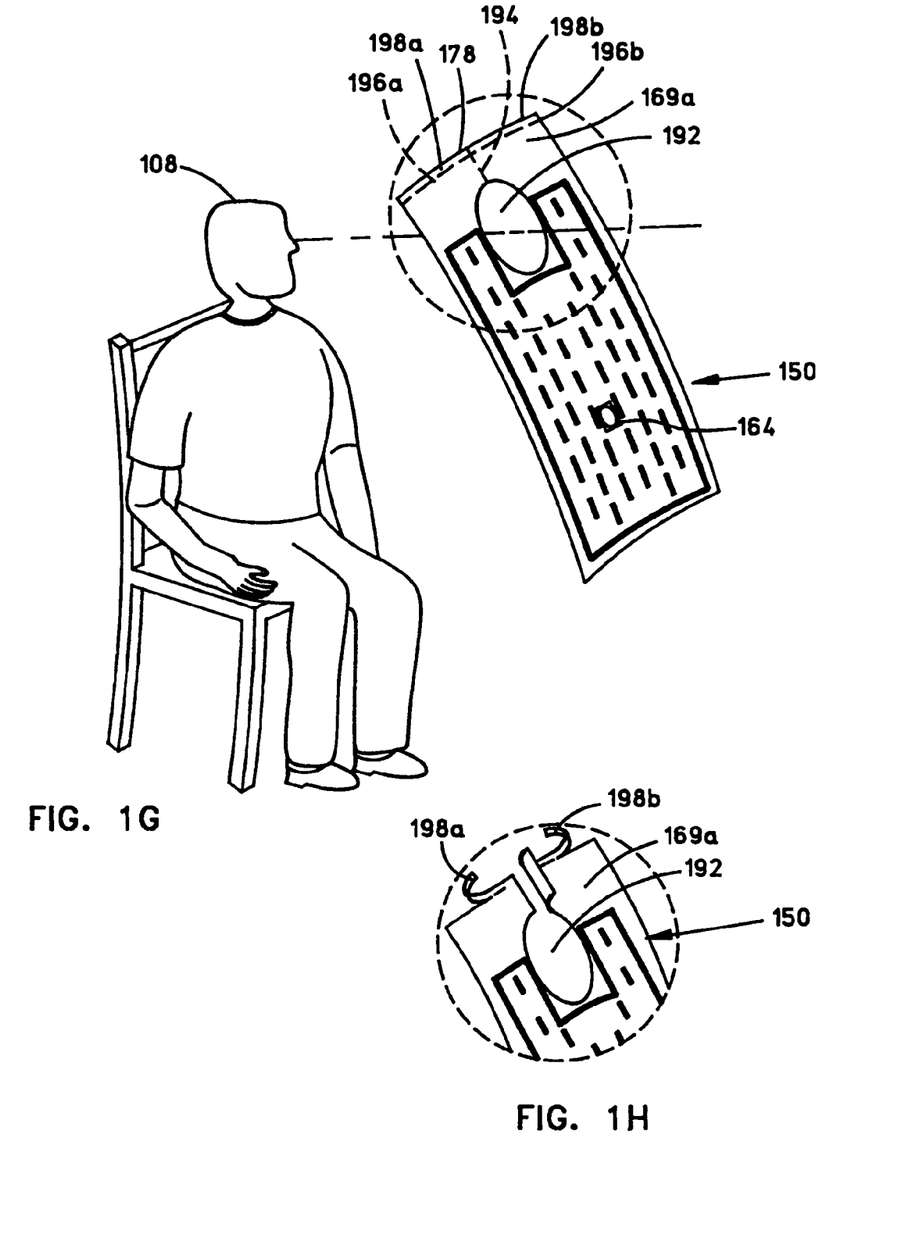
Figure 1I:
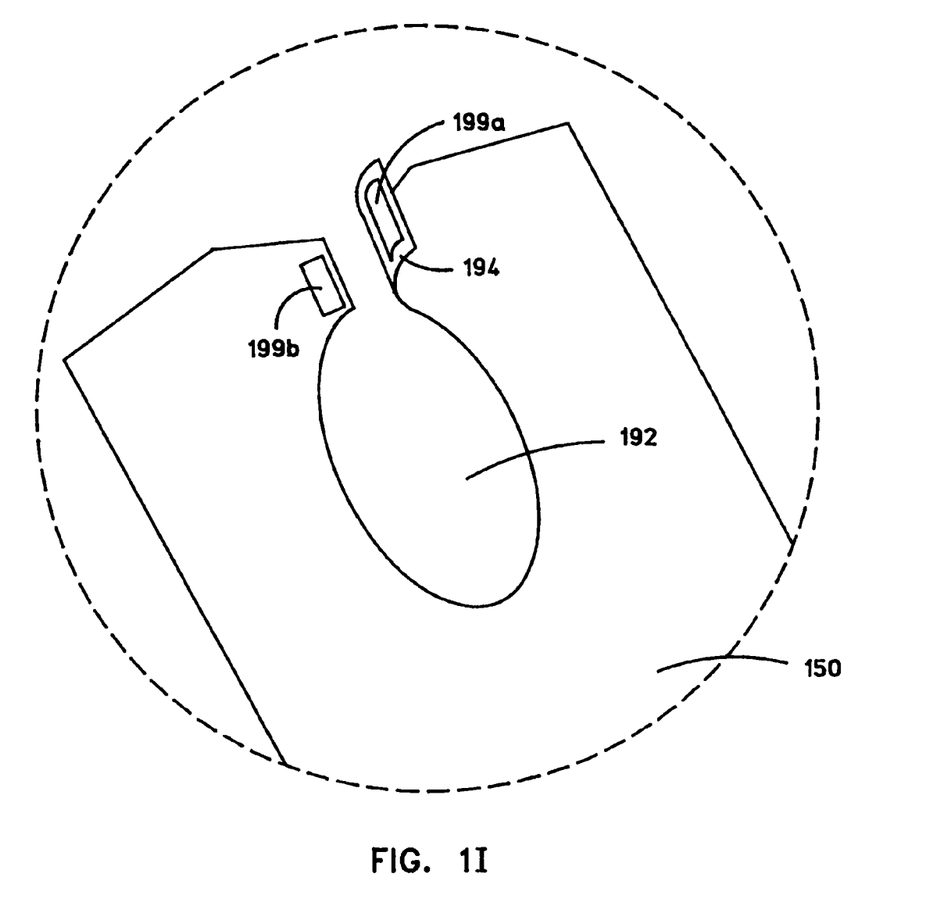
Figure 1J:
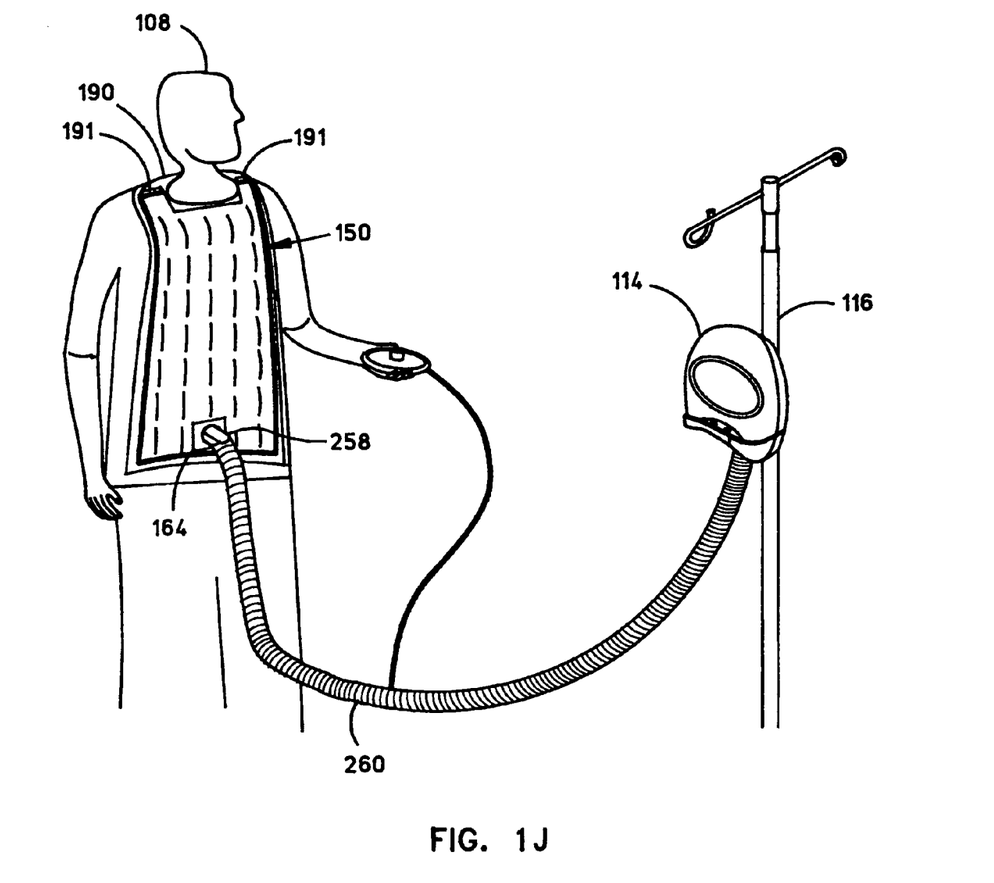
FIG. 1J is a perspective view drawing showing engagement of the combination in a warming system.

FIG. 1J illustrates a patient 108 in the standing position wearing the pneumatic convective device 150, as described above. The pneumatic convective device 150 may also be worn by a patient 108 in a sitting position, such as in FIG. 1G. The patient may be in a doctor's office in an out-patient facility, or any other suitable location. The pneumatic convective device 150 is shown how it would be attached to the patient. An end 258 of an air hose 260 is connected to the pneumatic convective device 150 may be received with the hose card 164 to provide a stream of pressurized, thermally treated air directed into the device 150 through inlet port 163. The other end of the air hose 258 is connected to a warming unit 114 that can provide a stream of pressurized, thermally controlled air to the device, like the one described in co-pending, concurrently filed patent application "FORCED AIR WARMING UNIT" which is incorporated herein by this reference. The temperature at the hose-end, prior to the air entering the pneumatic convective device 150, may range from ambient to 42° C. The average air temperature delivered to the patient may be less than this, depending on the gown design. The airflow at the hose-end, prior to the air entering the pneumatic convective device 150, may be between 5–15 CFM. The pressure inside the pneumatic convective device 150 may range of 0.25 to 0.75 inches $H_2O$. The warming unit 114 may be mounted on an IV pole 116, as illustrated.

When the stream of pressurized, thermally treated air is provided to the device 150, the device 150 tautens and air is emitted through the sheet 160, treating the person 108 with thermally controlled air. As can be appreciated with reference to FIG. 1J, with the pneumatic convective device 150 worn by a person 108, the device 150 is disposed so that the permeable sheet 160 faces the person 108 primarily in the chest region. Thus when pressurized, thermally treated air is provided to the device 150, it is distributed within the device, and emitted through the sheet 160, focusing or concentrating the emitted air primarily on the person's upper thorax. Convection will then cause heat transfer between the emitted, thermally treated air and the person's body core or diminish heat loss from the person's body to the environment.

Refer to FIG. 1C for an understanding of how the embodiment shown in FIGS. 1A and 1B may be constructed. The sheets 160 and 162 may have an identical laminate structure in which a layer (160a, 162a) of extruded synthetic material is lined with a layer (160b, 162b) of non-woven material. If a laminate structure is selected, holes or apertures 166 are formed through both layers 160a, 160b of the sheet 160. The sheets 160 and 162 are oriented to have the extruded layers (160a and 162a) facing, and the seals 168, 172 are formed by a gluing process or by a heating or ultrasonic process acting through one of the layers of non-woven material. Examples of non-woven material include any one or more of polyester, cotton, rayon, polypropylene, and wood pulp. Examples of extruded synthetic material include polypropylene, polyesters, and polyurethanes. Holes or apertures 166 may be formed during the process which joins the sheets 160 and 162

Figure 1K:
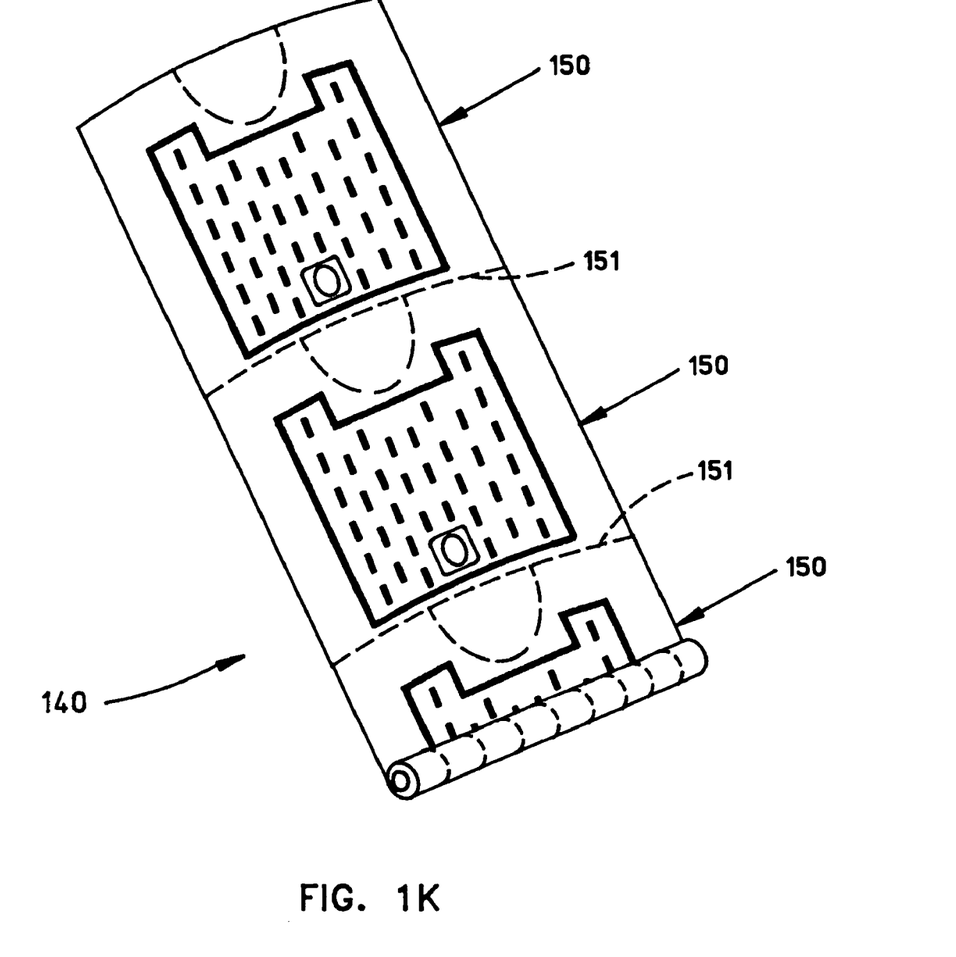
FIG. 1K shows the pneumatic convective device provided on a roll for dispensing.

One advantage of the embodiment disclosed is that the pneumatic convective devices may be provided to the user in bulk fashion, such as in sheet form, a dispenser box or on a roll 140, as shown in FIG. 1K. For example, the pneumatic convective devices 150 provided on a roll dispenser 140 may have perforated lines 151 separating each device. Users may simply select a new pneumatic convective devices 150 for application in the field, say in the patient's dressing room or at the patient's care site and separate it from the roll along the perforated lines 151. This allows for more cost-effective inventory storage and ease of accessibility.

Figure 2A:
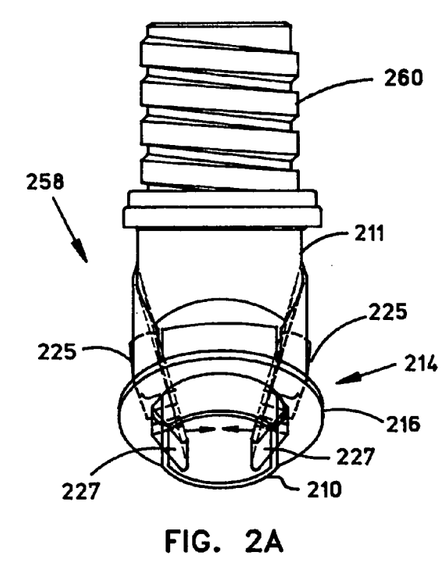
FIGS. 2A–2D illustrate an air hose coupling adapted for use with the pneumatic convective device of FIGS. 1A–1K.
Figure 2B:
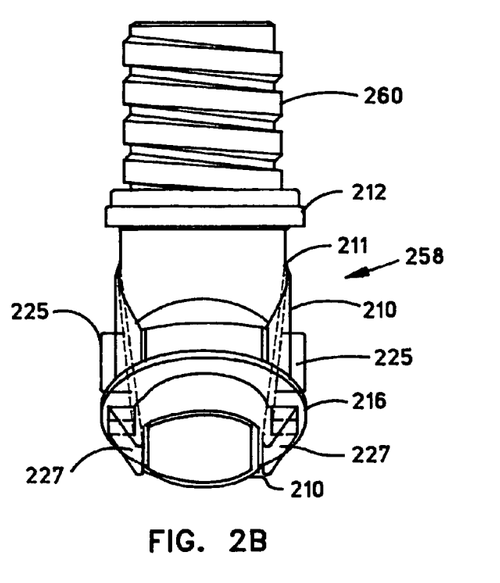
Figure 2C:
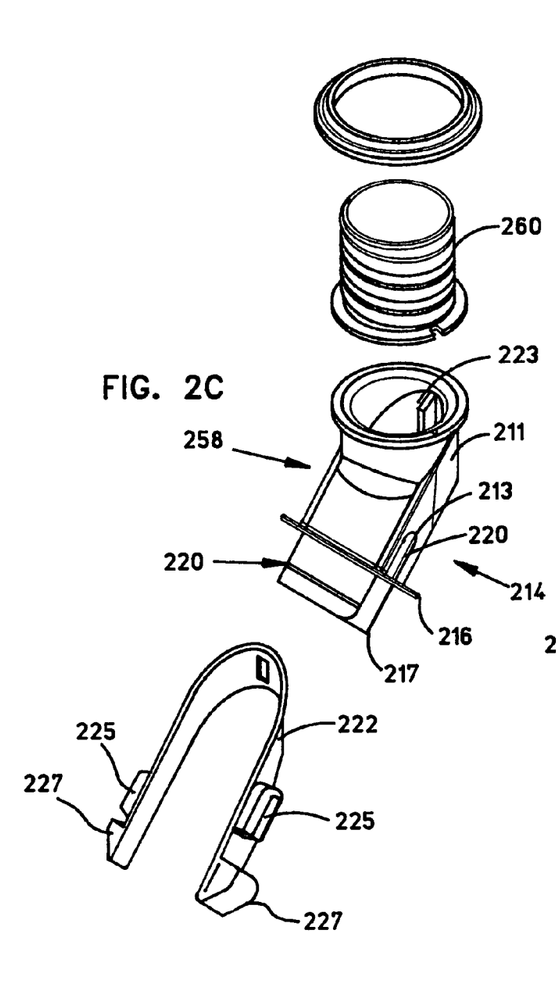
Figure 2D:
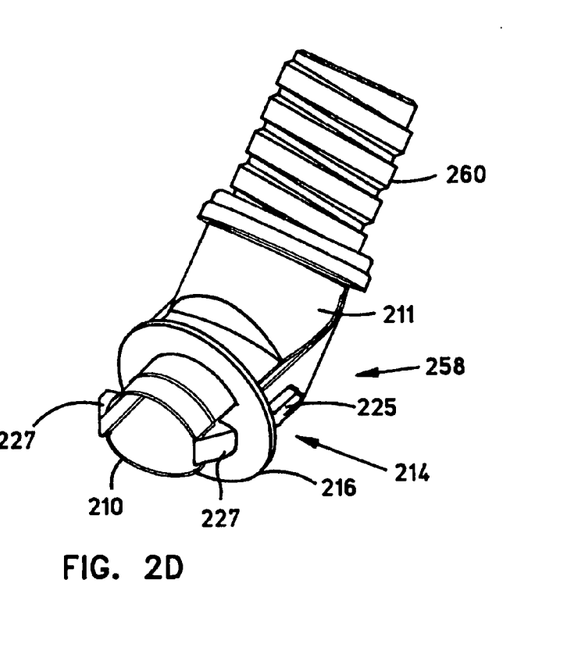

In FIGS. 2A–2D, an air hose 260 has an end 258, which is in the form of a nozzle 210 attached to the air hose 260 at an annular junction 212. The nozzle 210 may transition from a tubular rear section 211 through an angle less than 90° to a tubular forward section 214. It is desirable that the nozzle 210 be provided with a mechanism to releasably couple it with a hose card of the pneumatic convective devices of FIGS. 1A–1J. An example of such a mechanism is shown in these figures. Opposing slots 220 are cut longitudinally along the forward section 214 of the nozzle, extending to its end 217. An annular flange 216 is formed circumferentially around the forward section 214 seated over the slots 220, back from the end 217. A flexible U-shaped latch 222 comprising opposing tongs is mounted to the inside of the nozzle 210, extending from the end 217 where the tongs are received in the slots 220, to the end of the rear section 213 in which a groove 223 is cut to receive and seat the spring end of the U-shaped latch 222. Finger pieces 225 mounted on the outsides of the tongs are received in the slots 220, behind the annular flange 216. The tongs have wedge-shaped pieces 227 mounted to their ends, forward of the annular flange 216. As best seen in FIG. 2A, the tongs of the latch 222 flex together toward the interior of the nozzle, away from the slots 220 in response to pressure applied to the finger pieces 225. According to the illustration in FIG. 2B, when the pressure is released, the tongs spring back to the annular flange 216. With reference to FIG. 1J, in operation, the nozzle 210, on the end of the air hose 260 is brought to an inlet port 163, the tongs are flexed together as in FIG. 2A and the end of the forward section 214 is inserted into the inlet port 163 far enough for the annular flange 216 to abut the hose card 164. The flexing pressure on the tongs is released and the tongs spring back against the annular flange 216. The hose card is held between the wedge-shaped pieces 227 and the annular flange 216, thereby maintaining the air hose 260 engaged or coupled to the pneumatic convective device served by the input port 163. The nozzle 210 can be disengaged or decoupled from the device by squeezing the tongs of the latch 222 together and removing the forward section 214 of the nozzle from the inlet port 127.

Preferably, the diameter of the inlet port is larger than that of the nozzle to allow for easy entry of the nozzle. As the latch is engaged, the nozzle is secured against the inlet port perimeter and abuts the annular flange, thus securing the fit to reduce or eliminate air leakage where the inlet port and the nozzle are joined. The nozzle may also be configured to swivel to accommodate the diverse range of motion the devices will experience in various settings.

The embodiments that are illustrated and described above are meant to be representative, and not limiting, of our invention. Other variations and embodiments will be apparent to those skilled in the art upon reading this description. For example, the illustrations and description show a pneumatic convective device disposed on or at the front of a clinical garment for convectively warming the chest of a person. The pneumatic convective device could also be mounted to or disposed at the back or sides of the garment, or may be adapted, sized, or constructed to extend along more or less of the thorax than shown in the illustrated embodiments of this invention.

What is claimed is:

1. A pneumatic convective device, comprising:
   a distribution region for distributing a stream of pressurized air;
   an inlet in communication with the distribution region for receiving a stream of pressurized air;
   a permeable member for emitting pressurized air from the distribution region;
   a region in which air is not distributed;
   an aperture in the region for receiving the head of a person; and
   a mechanism acting with the aperture for releasably retaining the pneumatic convective device against the neck of the person;
   wherein the mechanism is a line of weakness in the region extending from a periphery to the aperture such that the region may be cloven into two opposing sections that may be separated to receive the person's neck and fastening means for releasably connecting two opposing sections around the person's neck.

2. The device of claim 1, wherein the permeable member emits pressurized air towards the person.

3. The device of claim 1, wherein the distribution region includes a first sheet and a second sheet sealed together continuously about a periphery.

4. The device of claim 3, wherein the permeable member is a portion of the first sheet.

5. The device of claim 3, wherein the inlet is located in the second sheet.

6. The device of claim 3, wherein the distribution region further includes attachment between the first and second sheets at multiple locations within the peripheries.

7. The device of claim 1, wherein the fastening means for releasably connecting is integral straps in the two opposing sections.

8. The device of claim 1, wherein the fastening means for releasably connecting is selected from the group consisting of Velcro buttons, string, snaps, repositionable adhesive, hook and eye elements, double-sided adhesive, hook and loop elements, rivets, and any and all equivalents thereof.

9. The device of claim 1, wherein the device is sized to cover the person's chest and the permeable member emits pressurized air toward the person's chest.

10. A patient comfort system, comprising:
    a pneumatic convective device having:
       a distribution region for distributing a stream of pressurized air;
       an inlet in communication with the distribution region for receiving a stream of pressurized air;
       a permeable member for emitting pressurized air from the distribution region;
       a region in which air is not distributed;
       an aperture in the region for receiving the neck of a person; and a mechanism acting with the aperture for releasably retaining the pneumatic convective device against the neck of the person;
wherein the mechanism is a line of weakness in the region extending from a periphery to the aperture such that the region may be cloven into two opposing sections that may be separated to receive the person's neck and fastening means for releasably connecting the two opposing sections around the person's neck;
a warming unit for providing the stream of pressurized air to the pneumatic convective device; and
an air hose for connecting the warming unit to the inlet.

11. The system of claim 10, wherein the system further includes means for releasably coupling the air hose to the inlet.

12. The system of claim 10, wherein the permeable member emits pressurized air towards the person.

13. The system of claim 10, wherein the distribution region includes a first sheet and a second sheet sealed together continuously along a periphery.

14. The system of claim 13, wherein the permeable member is a portion of the first sheet.

15. The system of claim 13, wherein the inlet is located in the second sheet.

16. The system of claim 13, wherein the distribution region further includes attachment between the first and second sheets at multiple locations within the peripheries.

17. The system of claim 10, wherein the fastening means for releasably connecting is integral straps in the two opposing sections.

18. The system of claim 10, wherein the fastening means for releasably connecting is selected from the group consisting of Velcro buttons, string, snaps, repositionable adhesive, hook and eye elements, double-sided adhesive, hook and loop elements, rivets, and any and all equivalents thereof.

19. The system of claim 10, wherein the pneumatic convective device is sized to cover a person's chest and the permeable member emits pressurized air toward the person's chest.

* * * * *

UNITED STATES PATENT AND TRADEMARK OFFICE
CERTIFICATE OF CORRECTION

PATENT NO.       : 7,001,416 B2
APPLICATION NO.  : 10/411865
DATED            : February 21, 2006
INVENTOR(S)      : Augustine et al.

Page 1 of 1

It is certified that error appears in the above-identified patent and that said Letters Patent is hereby corrected as shown below:

Title page,
Item [56], References Cited, U.S. PATENT DOCUMENTS,
"6,596,019" reference, delete "B1" and replace with -- B2 --.
"6,695,872" reference, delete "B1" and replace with -- B2 --.

Column 3,
Line 49, delete "maintain".

Column 7,
Line 7, insert -- . -- following "162".

Signed and Sealed this

Twentieth Day of June, 2006

JON W. DUDAS
*Director of the United States Patent and Trademark Office*